(12) United States Patent
Mathias et al.

(10) Patent No.: US 12,740,867 B2
(45) Date of Patent: Sep. 22, 2026

(54) PROSTHESES

(71) Applicant: INIXIO LIMITED, Sheffield (GB)

(72) Inventors: Rod Mathias, Sheffield (GB); Ivan Green, Sheffield (GB)

(73) Assignee: INIXIO LIMITED, Sheffield (GB)

( * ) Notice: Subject to any disclaimer, the term of this patent is extended or adjusted under 35 U.S.C. 154(b) by 584 days.

(21) Appl. No.: 18/249,374

(22) PCT Filed: Oct. 15, 2021

(86) PCT No.: PCT/GB2021/052680
§ 371 (c)(1), (2) Date: Apr. 17, 2023

(87) PCT Pub. No.: WO2022/084659
PCT Pub. Date: Apr. 28, 2022

(65) Prior Publication Data

US 2023/0397993 A1 Dec. 14, 2023

(30) Foreign Application Priority Data

Oct. 19, 2020 (GB) ..................................... 2016534

(51) Int. Cl.
*A61F 2/34* (2006.01)
*A61F 2/46* (2006.01)
*A61F 2/30* (2006.01)

(52) U.S. Cl.
CPC .................. *A61F 2/34* (2013.01); *A61F 2/46* (2013.01); *A61F 2002/30616* (2013.01); *A61F 2002/3456* (2013.01); *A61F 2002/4631* (2013.01); *A61F 2310/00179* (2013.01); *A61F 2310/00407* (2013.01); *A61F 2310/00796* (2013.01)

(58) Field of Classification Search
CPC ..... A61F 2/34; A61F 2/46; A61F 2002/30616
See application file for complete search history.

(56) References Cited

U.S. PATENT DOCUMENTS 3,641,590 A 2/1972 Michele
5,549,693 A * 8/1996 Roux .................... A61L 27/105 623/22.14

(Continued)

FOREIGN PATENT DOCUMENTS

DE 2751537 A1 5/1979
EP 0013863 A1 8/1980

(Continued)

OTHER PUBLICATIONS

International Search Opinion and Written Opinion received in PCT Application No. PCT/GB2021/052680 as mailed May 30, 2022 in 20 pages.

*Primary Examiner* — Vi X Nguyen
(74) *Attorney, Agent, or Firm* — Knobbe, Martens, Olson & Bear, LLP

(57) ABSTRACT

A set of ceramic acetabular cup prostheses (100) and ceramic femoral head prostheses (200) suitable for use therewith wherein the bearing diameter centre point of the cup is laterally offset from the outer diameter centre point of the cup along the longitudinal axis of the cup and wherein, for each cup in the set starting from the smallest cup in the set, the outer diameter increases in 2 mm increments and the inner diameter increases in less than 2 mm increments.

20 Claims, 2 Drawing Sheets

(56) References Cited

U.S. PATENT DOCUMENTS

| | | | | |
|---|---|---|---|---|
| 2003/0163202 | A1* | 8/2003 | Lakin .................... | A61F 2/3601 623/22.21 |
| 2016/0113771 | A1 | 4/2016 | McMinn | |
| 2020/0085582 | A1 | 3/2020 | Carrasco et al. | |

FOREIGN PATENT DOCUMENTS

| | | | |
|---|---|---|---|
| EP | 1360949 | A1 | 11/2003 |
| EP | 1433443 | A1 | 6/2004 |
| EP | 1611870 | A1 | 1/2006 |
| EP | 2174621 | A1 | 4/2010 |
| WO | WO 2009/076293 | A2 | 6/2009 |

* cited by examiner

PROSTHESES

This invention relates to a ceramic acetabular cup and a resurfacing head prosthesis for use in hip resurfacing surgery.

BACKGROUND

Hip resurfacing is an alternative to a conventional total hip replacement wherein both the head of a femur and the socket or the acetabulum are removed and replaced with prostheses. During hip resurfacing, only a few millimetres of the femur head are shaved down to accept a replacement head, whereas for the socket the procedure is similar to that of a hip replacement where a prosthetic acetabular cup is fixed in the acetabulum bone. Currently clinically available hip resurfacing prostheses include metal (metal-on-metal), ceramic (ceramic-on-ceramic) implants and their combination (ceramic-on-metal).

It is known that metal only prostheses can release metal wear particles into the human body and patients having metal-on-metal implants have to be regularly tested for the presence of metal ions in the blood stream. From this point of view, it is advantageous to use ceramics as an implant material as it has been demonstrated that ceramic prostheses are more biocompatible and/or biologically inert when implanted into the body.

The resurfacing heads are normally attached to the part of femur by means of forming a cement mantle inside the inner profile of the head. Occasionally, fixation failures may develop when too much prolonged stress is applied to the implant, which may occur during normal functioning of the joint. These stresses may cause loosening of the bone-cement interface and may lead to a malfunctioning of the joint resulting in implant failure.

Another problem associated with full or partial hip replacement is concerned with the relative sizes of the prosthetic head and cup. The desired cup and head size are usually determined by the size and height of the patient, and are normally smaller in females. Therefore a set of differently-sized prostheses is available to the surgeon, with both the outer diameter of the cup (which sits in the acetabulum) and the inner diameter of the cup (which fits snugly with a correspondingly sized head) typically increasing in 2 mm increments. In a hip resurfacing procedure, it is generally desirable to minimise the amount of natural bone that is removed in order to accommodate the implants. At the same time, it is desirable to maximise the head-to-neck ratio for the resurfaced femur. The resurfaced "head-to-neck ratio" is the ratio between the diameter of the resurfacing head and the diameter of the natural femoral neck. The head-to-neck ratio affects the range of motion for the resurfaced joint, which is desirably as great as possible. However, maximising the head-to-neck ratio for smaller femurs and achieving consistent scaling for the whole range of sizes is difficult to achieve.

It is therefore an object of embodiments of the invention to at least mitigate one or more of the problems associated with the prior art.

BRIEF SUMMARY OF THE DISCLOSURE

Aspects and embodiments of the invention provide a ceramic acetabular cup and a ceramic resurfacing head, as claimed in the appended claims.

In accordance with the present invention there is provided a set of differently-sized ceramic acetabular cup prostheses, each cup in the set comprising:

- a generally hemispherical outer surface having a cup pole with a longitudinal axis of the cup passing therethrough, an equatorial cup rim and an outer diameter having an outer diameter centre point ("COD");
- a generally hemispherical inner bearing surface having a bearing surface edge and a bearing diameter having a bearing diameter centre point ("CBD"); and
- a cup thickness defined between the inner bearing surface and the outer surface of the cup,
- wherein the CBD is laterally offset from the COD along the longitudinal axis and
- wherein, for each cup in the set starting from the smallest cup in the set, the outer diameter increases in 2 mm increments and the inner diameter increases in less than 2 mm increments.

Advantageously, such incrementation allows for an improved size variation of the cups, thus providing more cup size choices to the surgeons and allowing to take into account individual's morphology and thus eliminating a one-size-fits-all approach for the hip treatment strategy. The combination of the lateral offset and the difference in scaling of the outer and inner diameters of the cup, improves the range of motion of the resurfaced joint reduces the chance of impingement and potentially reduce wear on the prosthesis.

In an embodiment, the outer diameter is between 45 and 67 mm. In yet another embodiment, the inner diameter is between 39.9 and 60.8 mm. Advantageously, the range of sizes allow for better matching of the prosthesis and maintaining the desired range of movement for different patients.

In an embodiment, the cup rim comprises an outer edge and an inner edge. The cup rim preferably has an edge radius between said bearing surface edge and said cup rim inner edge, preferably an edge radius of at least 1 mm. Advantageously, such a configuration helps avoid irritation of the soft tissue traversing the cup rim, e.g. the psoas tendon.

In an embodiment, the lateral offset of the inner bearing surface is defined by fixed bearing arc of 160° measured from the CBD to the inner bearing surface edge. The lateral offset may be between 2.6 and 4.5 mm. Advantageously, the presence of the lateral offset leads to a translation of the geometric centre of rotation and, in turn, allows for better positioning of the acetabular cup in the acetabulum.

In an embodiment, the cup thickness is between 2.8 and 3.5 mm. Preferably, the cup thickness is greatest at the cup pole and thinnest at the cup rim. Advantageously, this helps minimise removal of the natural acetabulum when preparing it to receive the cup.

In an embodiment, the outer surface comprises a plasma-sprayed coating. In another embodiment, the plasma-sprayed coating comprises one or more of titanium and hydroxyapatite. Advantageously, the presence of a rough and partially porous coating allows for an improved initial cup fixation as well as subsequent osseointegration and long-term fixation due to the presence of a biocompatible ceramic Ca—P component (e.g. hydroxyapatite).

In an embodiment, the outer surface is flattened at the cup pole, preferably wherein the flattened section subtends an angle of 22° from the COD.

In another aspect of the present invention there is provided a ceramic femoral head prosthesis suitable for use with the ceramic cup prostheses comprising:

- a generally spherical outer bearing surface having an outer diameter and a head rim;

an inner socket having an inner surface configured for receiving a prepared femur, the inner socket surface comprising a first near-cylindrical portion nearest the head rim and a second tapered portion adjacent said first portion;

a head thickness defined between the inner surface and the outer bearing surface; and a stem projecting laterally inwardly from a pole of the inner surface along a longitudinal axis of the head, the stem having a proximal end and a distal end, wherein the distal end projects laterally beyond said head rim, wherein the first near-cylindrical portion comprises a first group of elongate cement pockets oriented generally parallel with and spaced around said longitudinal axis.

Advantageously, the presence of the cement pockets provides resistance to torque-out loads. The stem having its distal end laterally projecting from the rim allows for better engagement with the femur as well as improved alignment during implantation.

In an embodiment, the second tapered portion comprises a second group of elongate cement pockets spaced around said longitudinal axis. Advantageously, such a configuration allows for improved resistance to pull-off loads of the cemented head.

In another embodiment, said cement pockets are equispaced around said longitudinal axis. In yet another embodiment, said cement pockets have a maximum depth of between 0.6 and 1.5 mm. In yet another embodiment, said cement pockets have a concave radiused profile. Advantageously, this allows for better head-to-bone connection by means of more uniform distribution of the cement inside the inner socket of the head.

In an embodiment, said proximal end is cylindrical and wherein said distal end is tapered in the lateral direction.

In another embodiment, said stem projects between 1 and 5 mm laterally beyond said head rim.

In yet another embodiment, said head rim comprises an outer edge and an inner edge.

In an embodiment, the outer edge of the head rim has a radius of at least 0.8 mm. In another embodiment, the inner edge of the head rim has a radius of at least 0.5 mm.

In an embodiment, the head thickness is between 3 and 5 mm. In another embodiment, the head thickness at the head rim is 1.3 mm.

In an embodiment, the first near-cylindrical portion of the inner socket tapers with respect to the longitudinal axis by 1.25°. In another embodiment, the second tapered portion of the inner socket tapers with respect to the longitudinal axis by 35 to 45°.

In an embodiment, the distal end of the stem is curved with a radius of between 1.5 and 4 mm. In another embodiment, the stem has a diameter at its proximal end of between 7 and 9 mm.

In another aspect of the present invention there is provided a set of differently-sized ceramic femoral head prostheses, wherein for each head in the set starting from the smallest head, the outer diameter increases in less than 2 mm increments. Advantageously, introduction of the degree of scaling that is different from the currently existing prostheses allows for a minimal amount of femur and acetabulum to be replaced during the implantation, as well maximising the head-to-neck ratio of the resurfaced femur.

In another aspect of the present invention there is provided a resurfaced hip joint comprising a ceramic acetabular cup and a ceramic femoral head prosthesis, wherein said inner bearing surface of the cup is configured to receive said outer bearing surface of the head.

BRIEF DESCRIPTION OF THE DRAWINGS

One or more embodiments of the invention will now be described by way of example only, with reference to the accompanying drawings, in which.

DETAILED DESCRIPTION

Acetabular Cup

Figure 1:
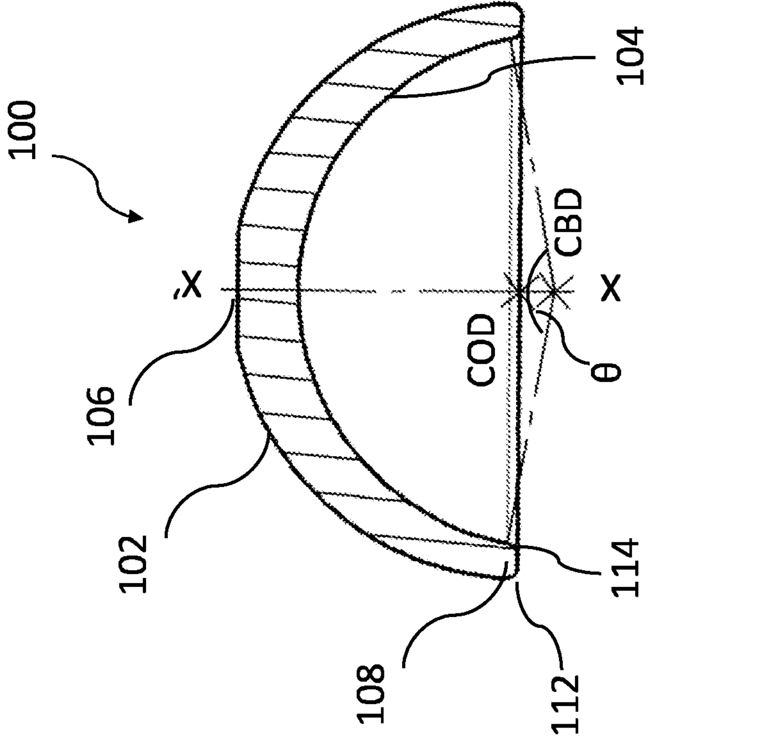
FIG. 1 shows an acetabular cup according to an embodiment of the invention.

FIG. 1 shows a cross-section of an acetabular cup 100 according to an embodiment of the invention. The cup has a generally hollow hemi-spherical shape and comprises an outer surface 102 and an inner bearing surface 104. The inner bearing surface 104 is intended to receive a resurfaced femoral head prosthesis (200 in FIG. 2) The inner surface 104 is highly polished and provides a snug fit between the cup 100 and the head 200. The outer surface 102 has an outer diameter that ranges between 45 mm to 67 mm and an outer diameter centre point (COD), wherein said diameter changes in 2 mm increments when scaling the size of the cup. The inner surface 104 has a bearing diameter in the range 39.9 mm and 60.8 mm and a bearing diameter centre point (CBD). The cup further comprises a cup pole 106 having a flattened profile with a longitudinal axis X-X' of the cup passing therethrough, and a cup rim 108 that is coplanar with the centre of the outside diameter (COD). The flattened profile of the cup pole is defined by an inclusive subtended angle of 17-22 degrees struck from the COD. The cup rim comprises an outer edge 112 and an inner edge 114, the cup rim 108 has an edge radius between said bearing surface 104 and said cup rim inner edge 114, preferably an edge radius is at least 1 mm to allow for a smooth movement of the femoral head 200 inside the cup 100. Optionally, the cup rim 108 may also have an edge radius of 1 mm between the outer surface 102 and the outer edge 112 of the rim 108 to avoid irritation of soft tissue traversing the rim.

The inner surface 104 is offset laterally from the cup pole 106. The lateral offset effectively translates the centre of hip rotation (in the resurfaced joint) laterally relative to the cup pole and this is desirable in maximising the range of motion in the resurfaced joint. The lateral offset of the inner bearing surface 104 is defined by a fixed bearing arc of 160° measured from a bearing diameter centre point CBD to the inner bearing surface edge. The lateral offset can be seen as an angle θ between two lines drawn from the centre of the bearing diameter CBD to the points marking the extent in each direction of the inner conforming bearing surface 104. As a result, the cup thickness is greatest at the cup pole 106 and thinnest at the cup rim 108. The fixed bearing arc and edge radius size effectively determine the degree of lateral offset of the bearing, which then scales with increasing bearing/cup size as a result. The resulting lateral offset values, measured from the cup rim 108 to the CBD, range from 2.6 mm to 4.5 mm between the smallest to largest size cups.

The outer surface 102 of the cup 100 may have a rough and partially porous plasma-sprayed dual coating of titanium and hydroxyapatite (HA). This provides both initial fixation (by "scratch-fit") as well as allowing enhanced longer term fixation following bone on-growth (osseointegration). The cup 100 is normally implanted into a prepared acetabulum reamed to between 1 and 2 mm smaller than the effective diameter of the coated surface 102.

A set of differently-sized acetabular cups is provided in order to accommodate the full range of differently sized patients. Whereas in a conventional acetabular cup set, their outer and inner diameters increase together in fixed increments, e.g. 2 mm, in the claimed cup set the ratio between the outer and inner diameters changes as one moves through the range of cups. Starting from the smallest cup in the set, the outer diameter increases in 2 mm increments whereas the inner diameter increases in smaller increments, e.g. 1.9 mm.

Femoral Head

Figure 2:
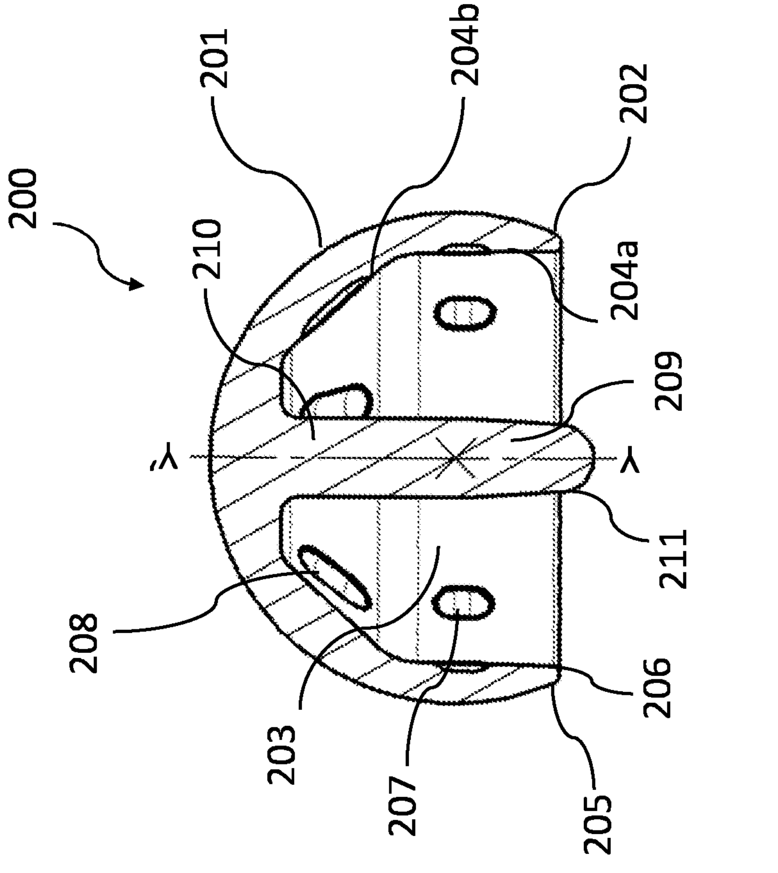
FIG. 2 shows a femoral head according to another embodiment of the invention.

FIG. 2 shows a monobloc ceramic femoral resurfacing head prosthesis 200. Said femoral head prosthesis is configured to be used with the ceramic cup 100 shown on FIG. 1 above, together forming the articulating joint of the resurfaced hip. The femoral head 200 is affixed to the patient's femur by cementing, and, like the acetabular cups, is provided in a range of sizes to suit individual patient anatomy. The head 200 comprises a generally spherical outer bearing surface 201 having an outer bearing diameter and a head rim 202. The bearing diameter is typically in the range 39.9 mm to 60.8 mm. The head 200 further comprises an inner socket 203 having an inner surface 204 intended to receive a prepared femur.

The inner surface 204 comprises two portions: a first near cylindrical portion 204*a* and a second tapered portion 204*b* adjacent to the first portion 204*a*. The first portion 204*a* tapers with respect to a longitudinal axis Y-Y' of the head by at least 1.25°, wherein the second tapered portion 204*b* tapers with respect to the longitudinal axis Y-Y' of the head by 35 to 45°. It is understood that the inner surface 204 and the outer surface 201 form a head thickness, that is defined as the furthest perpendicular distance between the first near-cylindrical portion 204*a* and the outer bearing surface 201, and lies in the range between 3 and 5 mm, depending on the size of the head 200. As a consequence of the head being generally spherical, the head thickness at the rim 202 lies in the range between 1.1 to 1.5 mm, preferably being 1.3 mm. It is important to conserve as much bone as possible on the natural femoral head and, in turn, for the head prosthesis wall thickness to be as thin as possible, particularly in the region nearest to the natural femoral neck.

As the outer bearing surface 201 is generally spherical, the head rim 202 forms a smooth radius between an outer edge 205 and an inner edge 206. Said radius has a size of at least 0.8 mm. Having a radiused rim helps avoid soft-tissue irritation and minimize edge wear. Furthermore, the inner edge 206 of the head rim 202 is also radiused, with the radius being at least 0.5 mm. The absence of sharp inner edges helps to avoid localised stress concentrations within the prosthesis. The outer bearing surface 201 and the rim edges 205 and 206 are highly polished for a better fit with the cup 100.

The first near-cylindrical portion 204*a* comprises a first group of elongate cement pockets 207 in the form of elongated recesses oriented generally parallel with and spaced, preferably equispaced, around the longitudinal axis Y-Y' of the head 200.

The second tapered portion 204*b* comprises a second group of cement pockets 208 that are regularly spaced around the longitudinal axis Y-Y'. Said first 207 and second 208 groups of cement pockets are elongated and between 0.6 and 1.5 mm in depth at their centers, with a concave radiused profile at each end running-up to the surrounding socket surface. It is also understood that other shapes of the cement pockets can be used, such as flat, square or trapezoid. While the second group of cement pockets 208 provides rotational stability, in a conventional manner by resisting rotation around the longitudinal axis Y-Y', the first group of pockets 207 provides a mechanical interlock with the cement mantle to resist both torsional and axial forces acting on the cemented femoral head 200. Therefore, as well as rotational stability, the cement pockets 207 also provide resistance to pull-off forces owing to their alignment with respect to the longitudinal axis Y-Y'. Advantageously, the pockets 207 provide a local high-point for cement ingress, deeper and further from the head's axis Y-Y' than the surrounding near-cylindrical inner portion 204.

The femoral head 200 further comprises a stem 209 projecting laterally inwardly from a pole of the inner surface 204 along the longitudinal axis Y-Y'. The stem 209 comprises a proximal end 210 and a distal end 211, said distal end projects laterally beyond the head rim 202. The stem 209 is of nearly-cylindrical shape and its diameter ranges in size between 7 and 9 mm. By "nearly-cylindrical" it is understood that the proximal end 210 of stem 209 is generally cylindrical, and the distal end 211 is tapered in the lateral direction. The length of the proximal portion can be 60-70% of the overall length of the stem 209. The stem 209 projects laterally between 1 and 5 mm, more preferably between 3 and 4 mm, beyond the level of the rim 202. The distal end 211 of the stem 209 is curved with a radius of between 1.5 and 4 mm.

The protruding distal end 211 of the stem 209 can be used to assist with the correct alignment of the femoral head 200 during implantation. It is understood that the stem 209 is intended to be a clearance fit within a prepared hole in the natural femur. In the other words, the natural femur is prepared to accept the inner socket 203 and the stem 209 of the resurfacing head 200 prior to cementing. The prepared natural femur has a profile which broadly resembles that of the inner socket 203, but leaving clearance between the natural bone and the fully-seated head 200 in some regions, in particular in the tapered portion 204*b*, to provide a maximum cement mantle thickness of approximately 0.5 mm.

A set of differently-sized femoral heads 200 is provided in order to accommodate the full range of differently sized patients. The bearing diameters of the differently-sized femoral heads increase in 1.9 mm increments through a range of 39.9 mm to 60.8 mm, in line with the inner diameters of the correspondingly-sized acetabular cups.

Prosthetic Joint Comprising an Acetabular Cup and a Femoral Head

Figure 3:
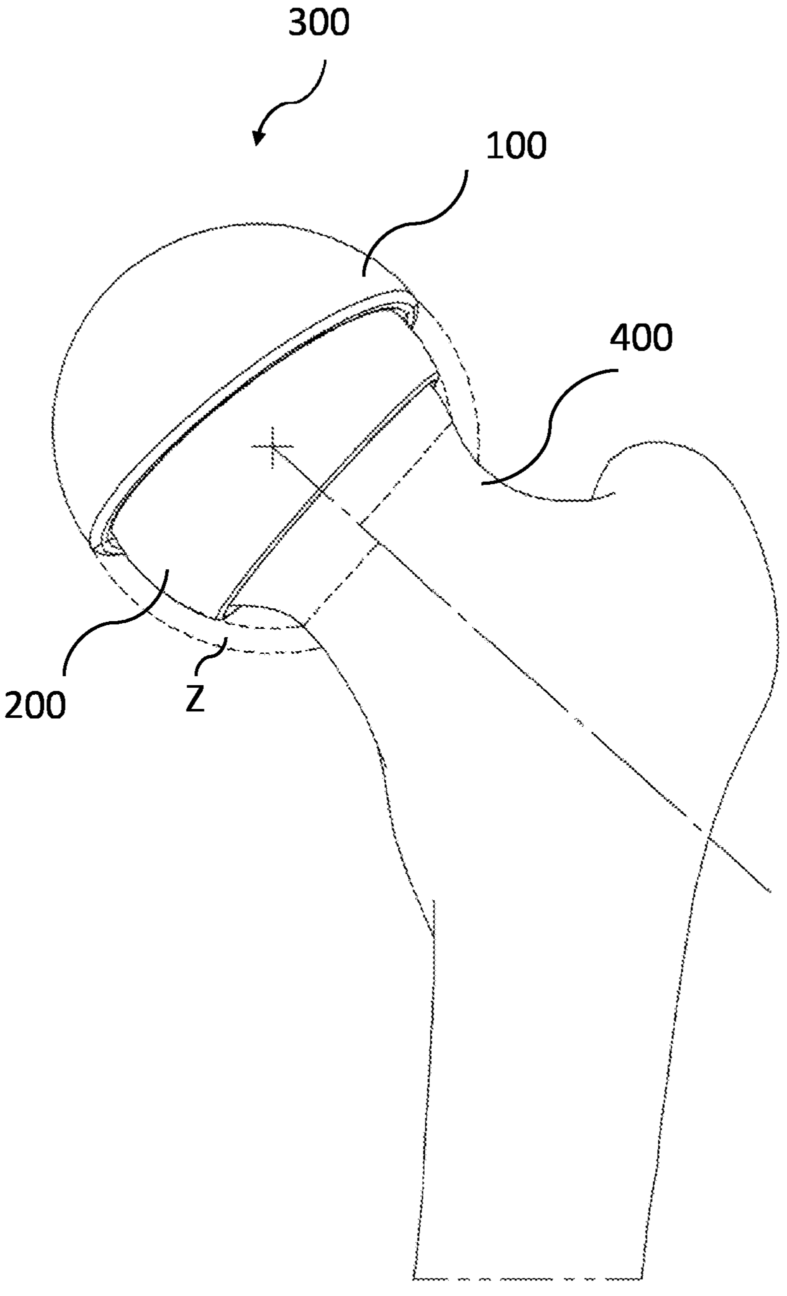
FIG. 3 shows a prosthesis according to another embodiment of the invention.

FIG. 3 shows a prosthetic hip joint 300 comprising an acetabular cup 100 and a femoral head 200, each selected from a set of available sizes. The prosthetic hip joint 300 is mounted on a natural femoral neck 400. As described above, starting from the smallest cup 100 in the set, the outer diameter thereof increases in 2 mm increments whereas the inner bearing diameter increases in smaller increments, e.g. 1.9 mm. The outer bearing diameter of the femoral head 200 matches the inner bearing diameter of the respective cup 100. This results in the ratio between the outer diameter of the cup and the bearing surface of the head being different for each size in the range. For example, for the smallest cup and head in the set, the ratio is 1.154. For the largest cup and head in the set, the ratio is 1.098.

FIG. 3 shows an impingement zone Z (indicated by dotted lines in FIG. 3) wherein rotation of the cup 100 on the head 200 is limited at the extremes by impingement on the natural femoral neck 400. The lateral offset of the inner surface of the cup 100 enables the cup 100 to rotate further with respect to the head 200 before impingement occurs. This effectively increases the range of motion in the resurfaced joint.

The variation in the ratio between the outer diameter of the cup 100 and the outer bearing surface of the head 200 contributes to desirably minimizing the amount of natural bone that needs to be removed to accommodate the prostheses (this having a greater adverse effect in a smaller sized patient). In addition, the variation in ratio contributes to maximising the head-neck ratio for the resurfaced femur. This, along with the lateral offset described above, maximises the range of motion of the resurfaced joint.

Throughout the description and claims of this specification, the words "comprise" and "contain" and variations of them mean "including but not limited to", and they are not intended to (and do not) exclude other additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The invention claimed is:

1. A set of differently-sized ceramic acetabular cup prostheses, each cup in the set comprising:

a generally hemispherical outer surface having a cup pole with a longitudinal axis of the cup passing therethrough, an equatorial cup rim and an outer diameter having an outer diameter centre point ("COD");

a generally hemispherical inner bearing surface having a bearing surface edge and a bearing diameter having a bearing diameter centre point ("CBD"); and a cup thickness defined between the inner bearing surface and the outer surface of the cup, wherein the CBD is laterally offset from the COD along the longitudinal axis and wherein, for each cup in the set starting from a smallest cup in the set, the outer diameter increases in 2 mm increments and the inner diameter increases in less than 2 mm increments.

2. The set of acetabular cup prostheses of claim 1, wherein the outer diameter is between 45 and 67 mm and/or the inner diameter is between 39.9 and 60.8 mm.

3. The set of acetabular cup prostheses of claim 1, wherein the cup rim comprises an outer edge and an inner edge.

4. The set of ceramic acetabular cup prostheses of claim 1, wherein the cup rim has an edge radius of 1 mm between said bearing surface edge and said cup rim inner edge, preferably an edge radius.

5. The set of ceramic acetabular cup prostheses of claim 1, wherein the lateral offset of the inner bearing surface is defined by a fixed bearing arc of 160° measured from the CBD to the inner bearing surface edge.

6. The set of ceramic acetabular cup prostheses of claim 1, wherein the lateral offset is between 2.6 and 4.5 mm and/or the cup thickness is between 2.8 and 3.5 mm.

7. The set of ceramic acetabular cup prostheses of claim 1, wherein the cup thickness is greatest at the cup pole and thinnest at the cup rim.

8. The set of ceramic acetabular cup prostheses of claim 1, wherein the outer surface comprises a plasma-sprayed coating comprises titanium and/or hydroxyapatite.

9. The set of ceramic acetabular cup prostheses of claim 1, wherein the outer surface is flattened at the cup pole to form a flattened section, preferably wherein the flattened section subtends an angle in the range 17-22° from the COD.

10. A ceramic femoral head prosthesis suitable for use with the set of ceramic cup prostheses of claim 1, comprising:

a generally spherical outer bearing surface having an outer diameter and a head rim;

an inner socket having an inner surface configured for receiving a prepared femur, the inner socket surface comprising a first near-cylindrical portion nearest the head rim and a second tapered portion adjacent said first portion;

a head thickness defined between the inner surface and the outer bearing surface; and a stem projecting laterally inwardly from a pole of the inner surface along a longitudinal axis of the head, the stem having a proximal end and a distal end, wherein the distal end projects laterally beyond said head rim, wherein the first near-cylindrical portion comprises a first group of elongate cement pockets oriented generally parallel with and spaced around said longitudinal axis.

11. The ceramic femoral head prosthesis of claim 10 wherein the second tapered portion comprises a second group of elongate cement pockets spaced around said longitudinal axis and the first group of cement pockets are equispaced around said longitudinal axis.

12. The ceramic femoral head prosthesis of claim 10, wherein said cement pockets have a concave radiused profile and a maximum depth of between 0.6 and 1.5 mm.

13. The ceramic femoral head prosthesis of claim 10, wherein said proximal end is cylindrical and wherein said distal end is tapered in the lateral direction.

14. The ceramic femoral head prosthesis of claim 10, wherein said stem projects between 1 and 5 mm laterally beyond said head rim.

15. The ceramic femoral head prosthesis of claim 10, wherein said head rim comprises an outer edge and an inner edge, the outer head having a radius of at least 0.8 mm and the inner edge of the head rim having a radius of at least 0.5 mm.

16. The ceramic femoral head prosthesis of claim 10, wherein the head thickness is between 3 and 5 mm and the thickness at the head rim is 1.3 mm.

17. The ceramic femoral head prosthesis of claim 10, wherein the first near-cylindrical portion of the inner socket tapers with respect to the longitudinal axis by 1.25° and the second tapered portion of the inner socket tapers with respect to the longitudinal axis by 35 to 45°.

18. The ceramic femoral head prosthesis of claim 10, wherein the distal end of the stem is curved with a radius of between 1.5 and 4 mm and a diameter at its proximal end of between 7 and 9 mm.

19. A set of differently-sized ceramic femoral head prostheses, comprising the ceramic femoral head prosthesis of claim 10, wherein for each head in the set starting from a smallest head, the outer diameter increases in less than 2 mm increments.

20. A resurfaced hip joint comprising the ceramic acetabular cup prostheses of claim 19, wherein said inner bearing surface of the cup is configured to receive an outer bearing surface of a ceramic femoral head prosthesis.

* * * * *